US011937952B2

(12) United States Patent
Eslava et al.

(10) Patent No.: US 11,937,952 B2
(45) Date of Patent: Mar. 26, 2024

(54) ROTATING DOCKING STATION (71) Applicant: Drägerwerk AG & Co. KGaA, Lübeck (DE)

(72) Inventors: Juan Pablo Eslava, Groton, MA (US); Zachary K. Hennings, Reading, MA (US); Peter Andrew Lund, Nashua, NH (US)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 60 days.

(21) Appl. No.: 17/348,634

(22) Filed: Jun. 15, 2021

(65) Prior Publication Data
US 2021/0307704 A1 Oct. 7, 2021

Related U.S. Application Data (63) Continuation of application No. 16/838,232, filed on Apr. 2, 2020, now Pat. No. 11,058,366, which is a continuation of application No. 16/224,423, filed on Dec. 18, 2018, now Pat. No. 10,646,170.

(60) Provisional application No. 62/608,493, filed on Dec. 20, 2017.

(51) Int. Cl.
*A61B 5/00* (2006.01)
*G16H 40/63* (2018.01)
*A61B 5/0205* (2006.01)

(52) U.S. Cl.
CPC ........... *A61B 5/7445* (2013.01); *G16H 40/63* (2018.01); *A61B 5/0205* (2013.01); *A61B 2560/0431* (2013.01); *A61B 2560/045* (2013.01); *A61B 2560/0456* (2013.01)

(58) Field of Classification Search
None
See application file for complete search history.

(56) References Cited

U.S. PATENT DOCUMENTS

| | | | | |
|---|---|---|---|---|
| 5,790,375 A | * | 8/1998 | Lee ..................... | G06F 1/1632 361/726 |
| 6,183,417 B1 | * | 2/2001 | Geheb .................. | G16H 40/63 600/301 |
| 6,716,058 B2 | * | 4/2004 | Youn .................... | G06F 1/1632 439/31 |
| 7,738,238 B2 | * | 6/2010 | Liu ........................ | H04N 5/64 361/679.01 |
| 8,780,546 B2 | * | 7/2014 | Zhou .................... | H01R 27/00 361/679.41 |
| 9,131,904 B2 | * | 9/2015 | Qualey ................ | A61B 5/002 |
| 9,153,112 B1 | * | 10/2015 | Kiani ................ | A61B 5/02438 |
| 9,182,786 B2 | * | 11/2015 | Meertens ............. | G06F 1/1632 |
| 9,207,714 B2 | * | 12/2015 | Boomhour ............ | H04M 1/04 |
| 9,429,994 B1 | * | 8/2016 | Vier ..................... | G06F 1/1632 |
| 9,760,116 B2 | * | 9/2017 | Wylie .................. | G06F 1/1654 |

(Continued)

Primary Examiner — Xanthia C Relford
(74) Attorney, Agent, or Firm — Nolte Lackenbach Siegel (57) ABSTRACT An apparatus includes a base component having a center axis and at least two index positions. The apparatus also includes a rotational component coupled to the base component. The rotational component is configured to circularly maneuver about the center axis between the at least two index positions. A docking receptacle of the apparatus is coupled to the rotational component and is configured to receive a monitor having an electronic visual display. The apparatus also includes a handle configured to facilitate maneuvering of the rotational component.

16 Claims, 8 Drawing Sheets (56) References Cited

U.S. PATENT DOCUMENTS

| | | | | |
|---|---|---|---|---|
| 9,845,912 B2 * | 12/2017 | Phillips | | H05K 7/18 |
| 9,891,666 B2 * | 2/2018 | Buss | | H01R 13/6315 |
| 9,973,013 B2 * | 5/2018 | Yan | | H02J 7/14 |
| 10,101,770 B2 * | 10/2018 | Schatz | | G06F 1/1632 |
| 2002/0082479 A1 * | 6/2002 | Frangesch | | A61B 5/00 |
| | | | | 600/300 |
| 2003/0167074 A1 * | 9/2003 | Merry | | A61N 1/3968 |
| | | | | 607/5 |
| 2005/0288571 A1 * | 12/2005 | Perkins | | A61B 5/742 |
| | | | | 600/407 |
| 2006/0104018 A1 * | 5/2006 | Tracy | | G06F 1/1632 |
| | | | | 361/679.55 |
| 2006/0171044 A1 * | 8/2006 | Carnevali | | G02B 25/005 |
| | | | | 359/802 |
| 2006/0229502 A1 * | 10/2006 | Pollock | | G06F 1/1626 |
| | | | | 436/95 |
| 2008/0273734 A1 * | 11/2008 | Solland | | H04R 1/02 |
| | | | | 381/334 |
| 2009/0009957 A1 * | 1/2009 | Crooijmans | | G06F 1/1632 |
| | | | | 361/679.41 |
| 2010/0108828 A1 * | 5/2010 | Yu | | F16M 11/041 |
| | | | | 248/123.11 |
| 2010/0179408 A1 * | 7/2010 | Kamath | | A61B 5/14546 |
| | | | | 600/365 |
| 2010/0261979 A1 * | 10/2010 | Kiani | | A61B 5/0002 |
| | | | | 600/301 |
| 2011/0075349 A1 * | 3/2011 | Ma | | G06F 1/1632 |
| | | | | 361/679.41 |
| 2012/0175474 A1 * | 7/2012 | Barnard | | F16M 11/14 |
| | | | | 248/122.1 |
| 2012/0273630 A1 * | 11/2012 | Gillespie-Brown | | |
| | | | | F16M 11/105 |
| | | | | 248/122.1 |
| 2013/0026322 A1 * | 1/2013 | Wheeler | | F16M 13/02 |
| | | | | 248/288.11 |
| 2013/0107449 A1 * | 5/2013 | Su | | F16M 13/00 |
| | | | | 361/679.56 |
| 2013/0202269 A1 * | 8/2013 | Rossiter | | H04N 5/765 |
| | | | | 386/230 |
| 2013/0262730 A1 * | 10/2013 | Al-Ali | | A61B 5/746 |
| | | | | 710/303 |
| 2014/0168884 A1 * | 6/2014 | Wylie | | G06F 1/1632 |
| | | | | 361/679.43 |
| 2014/0201414 A1 * | 7/2014 | Keegan | | G06F 13/4081 |
| | | | | 710/303 |
| 2015/0362953 A1 * | 12/2015 | Shindo | | G06F 1/1632 |
| | | | | 361/679.41 |
| 2016/0224065 A1 * | 8/2016 | Weldon | | G06F 1/1632 |
| 2016/0255531 A1 * | 9/2016 | Stein | | H04W 12/50 |
| | | | | 455/575.1 |
| 2016/0309010 A1 * | 10/2016 | Carnevali | | H04M 1/185 |
| 2016/0352382 A1 * | 12/2016 | Andrus | | H04M 1/04 |
| 2018/0080597 A1 * | 3/2018 | Weldon | | G06F 1/1632 |
| 2021/0120690 A1 * | 4/2021 | Stalter | | A61B 8/56 |

* cited by examiner

ROTATING DOCKING STATION

CROSS REFERENCE TO RELATED APPLICATIONS

This application claims priority to U.S. Application No. 62/608,493, filed Dec. 20, 2017; U.S. application Ser. No. 16/224,423, filed Dec. 18, 2018 and U.S. application Ser. No. 16/838,232, filed Apr. 2, 2020 the contents of which are incorporated herein by reference in their entirety.

TECHNICAL FIELD

The subject matter described herein relates generally to a rotatable docking station for use in connection with a patient monitor.

BACKGROUND

During the course of providing healthcare to patients, practitioners typically monitor patient medical parameters of a patient using a monitoring device. These are usable by healthcare practitioners (e.g., nurses, doctors, physician assistants, or any other person charged with providing a healthcare service to a patient) in monitoring a patient and determining a course of healthcare to be provided to the patient. Patient monitoring devices can be selectively connected to the patients at any point during which a healthcare professional comes into contact with the patient and thus can remain connected with the patient as the patient moves through various locations within a particular healthcare enterprise (e.g. hospital) or between different healthcare enterprises (e.g. different medical facilities). Once it is determined that a patient is to remain in a fixed location, the patient monitoring devices are selectively connected (docked) to a docking station that can serve as a gateway for connecting the patient monitoring device to a hospital information system (HIS) and/or central monitoring station and allowing data representing the at least one patient medical parameter to be communicated to other systems within the healthcare enterprise.

SUMMARY

In one aspect, an apparatus includes a base component having a center axis and at least two index positions, a rotational component coupled to the base component configured to circularly maneuver about the center axis between the at least two index positions, a docking receptacle coupled to the rotational component configured to receive a monitor having an electronic visual display, and a handle configured to facilitate maneuvering of the rotational component.

In some variations, the monitor can be a patient monitoring device. The patient monitoring device can be coupled to at least one physiological sensor measuring one or more physiological parameters of a patient. The one or more physiological parameters can be provided by the at least one physiological sensor. The patient monitoring device can be configured to display one or more physiological parameters provided by the at least one physiological sensor on the electronic visual display.

In other variations, the apparatus can further include a power supply internal to the base component configured to provide power to the monitor when docked in the docking receptacle.

In some variations, the apparatus can further include an index mechanism having a locking component. The index mechanism can be configured to engage the locking component to selectively maintain a position of the rotational component at one of the at least two index positions. The index mechanism can disengage the locking component based on a user interacting with the handle. The user interacting with the handle can include gripping the handle. Alternatively, the user interacting with the handle can include touching the handle. The handle can be configured to receive a grip from a male user or a female user having an anthropometric profile between a fifth percentile and a ninety-fifth percentile.

In other variations, the apparatus can further include a sliding shroud configured to cover the docking receptacle in absence of the monitor being docked. The sliding shroud can protect a docking connector within the docking receptacle. The sliding shroud can be further configured to retract away from the docking receptacle.

In some variations, the rotational component can be further configured to prohibit movement to one of the at least two index positions based on the monitor being docked in the docking receptacle. The at least two index positions can be spatially separated indices of about 90 degrees. The at least two index positions can be defined by magnetic positional stops. Alternatively, the at least two index positions can be defined by mechanical positional stops.

In other variations, the base component, rotational component, the docking receptacle, and the handle can each include ergonomic radii to facilitate cleaning about the ergonomic radii.

In some variations, the apparatus can further include an electrical connection to the base component configured to provide power to the monitor.

In other variations, the apparatus can further include an electrical connection to the base component configured to facilitate transmission of data to the monitor.

In some variations, the base component can further include at least three index positions.

The details of one or more variations of the subject matter described herein are set forth in the accompanying drawings and the description below. Other features and advantages of the subject matter described herein will be apparent from the description and drawings, and from the claims.

The subject matter described herein provides many technical advantages. For example, the rotatable docking station as described herein provides positioning of a docking station in various index positions without having to move the entire docking station. A rotatable component of the docking station, as described herein, provides for docking of a patient monitor in one or more index positions facilitating right and left handed docking. Additionally, an ergonomic handle design allows for such rotation to be made by a user using a single hand.

DESCRIPTION OF DRAWINGS

Like reference symbols in the various drawings indicate like elements.

DETAILED DESCRIPTION

Selectively docking a patient monitoring device to a docking station can allow for power and/or data transmission between the patient monitoring device and the docking station. A rotatable docking station can provide for docking of a patient monitoring device in various index positions to facilitate usability of the docked monitor. More specifically, the rotating docking station can have a rotatable component that can be circularly maneuvered about a 360 degree rotational axis using a mechanical or magnetic index mechanism.

Figure 1:
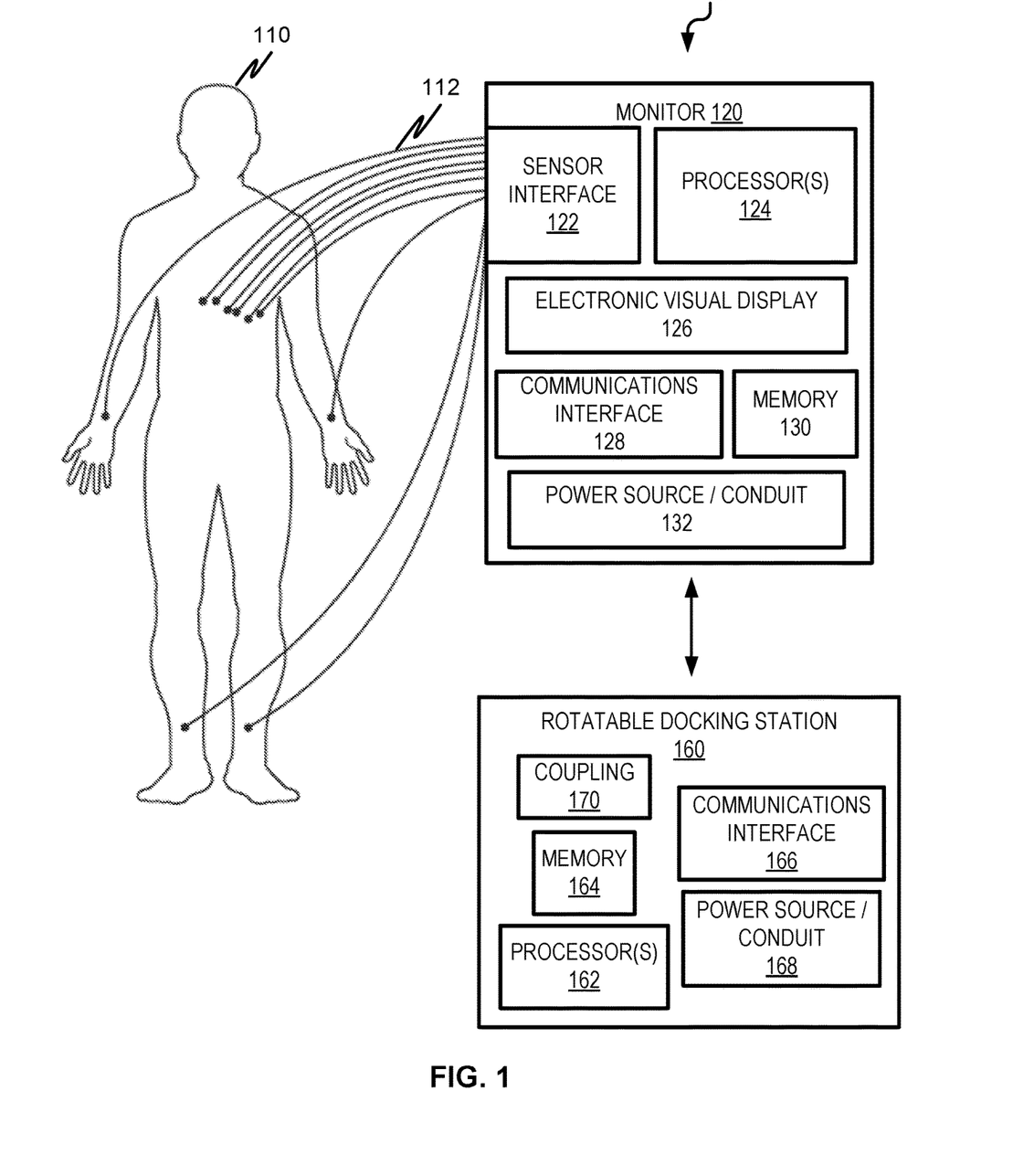
FIG. 1 is a logic diagram illustrating a monitor and a rotatable docking station.

FIG. 1 is a logic diagram 100 illustrating a monitor 120 and a rotatable docking station 160. FIGS. 2, 4-8 are diagrams providing various views 200, 400-800 of example implementations of the monitor 120 and the rotatable docking station 160. While certain configurations are illustrated with regard to the rotatable docking station 160 and the monitor 120, it will be appreciated that these illustrations in FIGS. 2 and 4-8 are examples and not limiting in nature (unless otherwise specified).

The monitor 120 can, for example, be a patient monitor that is used to monitor various physiological parameters for a patient2 110. With such a variation, the monitor 120 can include a sensor interface 122 that can be used to connect via wired and/or wireless interfaces to one or more physiological sensors and/or medical devices via one or more cables 112 (e.g., ECG electrodes, SPO2 sensor, blood pressure cuffs, apnea detection sensors, respirators, etc.) associated with the patient 110. The monitor 120 can include one or more processors 124 (e.g., programmable data processors, etc.) which can execute various instructions stored in memory 130 of the monitor 120. Various data and graphical user interfaces can be conveyed to a user via an electronic visual display 126. This information can, for example, relate to the measured physiological parameters of the patient 110 and the like (e.g., blood pressure, heart related information, pulse oximetry, respiration information, etc.). Other types of information can also be conveyed by the electronic visual display 126. In some variations, the electronic visual display 126 includes a touch screen interface.

The monitor 120 can additionally include a communications interface 128 which allows the monitor 120 directly or indirectly (via, for example, the rotatable docking station 160) to access one or more computing networks. The communications interface 128 can include various network cards/interfaces to enable wired and wireless communications with such computing networks. The communications interface 128 can also enable direct (i.e., device-to-device, etc.) communications (i.e., messaging, signal exchange, etc.) such as from the rotatable docking station 160 to the monitor 120.

The monitor 120 can optionally also include a power source and/or conduit 132 that can be used to power the various components of the monitor 120. The power source/conduit 132 can include a self-contained power source such as a battery pack and/or it can include an interface to be powered through an electrical outlet (either directly or by way of the rotatable docking station 160).

The rotatable docking station 160 can include one or more processors 162 (e.g., programmable data processors, etc.) which can execute various instructions stored in memory 164 of the rotatable docking station 160. The rotatable docking station 160 can additionally include a communications interface 166 which allows the rotatable docking station 160 directly or indirectly to access one or more computing networks. The communications interface 166 can include, various network cards/interfaces to enable wired and wireless communications with such computing networks. The communications interface 166 can also enable direct (i.e., device-to-device, etc.) communications (i.e., messaging, signal exchange, etc.) such as with the monitor 120.

The rotatable docking station 160 can optionally also include a power source and/or conduit 168 that can be used to power the various components of the rotatable docking station 160 and/or the monitor 120 when secured to the rotatable docking station 160. The power source/conduit 168 can include a self-contained power source such as a battery pack and/or it can include an interface to be powered through an electrical outlet.

In some variations, the processors 162 and the memory 164 are omitted such that the rotatable docking station 160 provides only physical support and optionally a power source.

The rotatable docking station 160 has a shape and size which allows it to detachably secure the monitor 120. In this regard, detachably secure means that the rotatable docking station 160 can secure the monitor 120 such that it can be removed by a user when desired.

The rotatable docking station 160 can include a coupling 170 that allows the monitor 120 to be secured at such location. The coupling 170 can include a combination of ledges, rails, ribs, abutments, latches, and the like to allow the monitor 120 to be secured to the rotatable docking station 160. The coupling 170 can additionally or alternatively use different securing mechanisms including magnetic and/or electromagnetic locking mechanisms which cause the monitor 120 to selectively be secured by the rotatable docking station 160. In some cases, the monitor 120 can slide into and out of the coupling 170 from a lateral direction (i.e., from the side of the rotatable docking station 160) while in other variations, the monitor 120 can be placed on and removed from the forward face of the rotatable docking station 160. In some implementations, the monitor 120 can both slide into and out of the coupling 170 from the lateral direction and be placed on and removed from the forward face of the rotatable docking station 160.

The positioning of the monitor 120, when secured to the rotatable docking station 160, can be such that the communications interface 128 on the monitor 120 lines up to the communications interface 166 of the rotatable docking station 160 to allow, for example, a direct electrical connection. In other variations, the communications interface 128 of the monitor 120 exchanges data with the communications interface 166 of the rotatable docking station 160 optically (via, for example, respective optical windows on the monitor 120 and the rotatable docking station 160).

The positioning of the monitor 120 when secured to the rotatable docking station 160 can also align the power source/conduit 132 of the monitor 120 to be coupled to the power source/conduit 168 of the rotatable docking station 160 which causes the rotatable docking station 160 to power the monitor 120.

Figure 2:
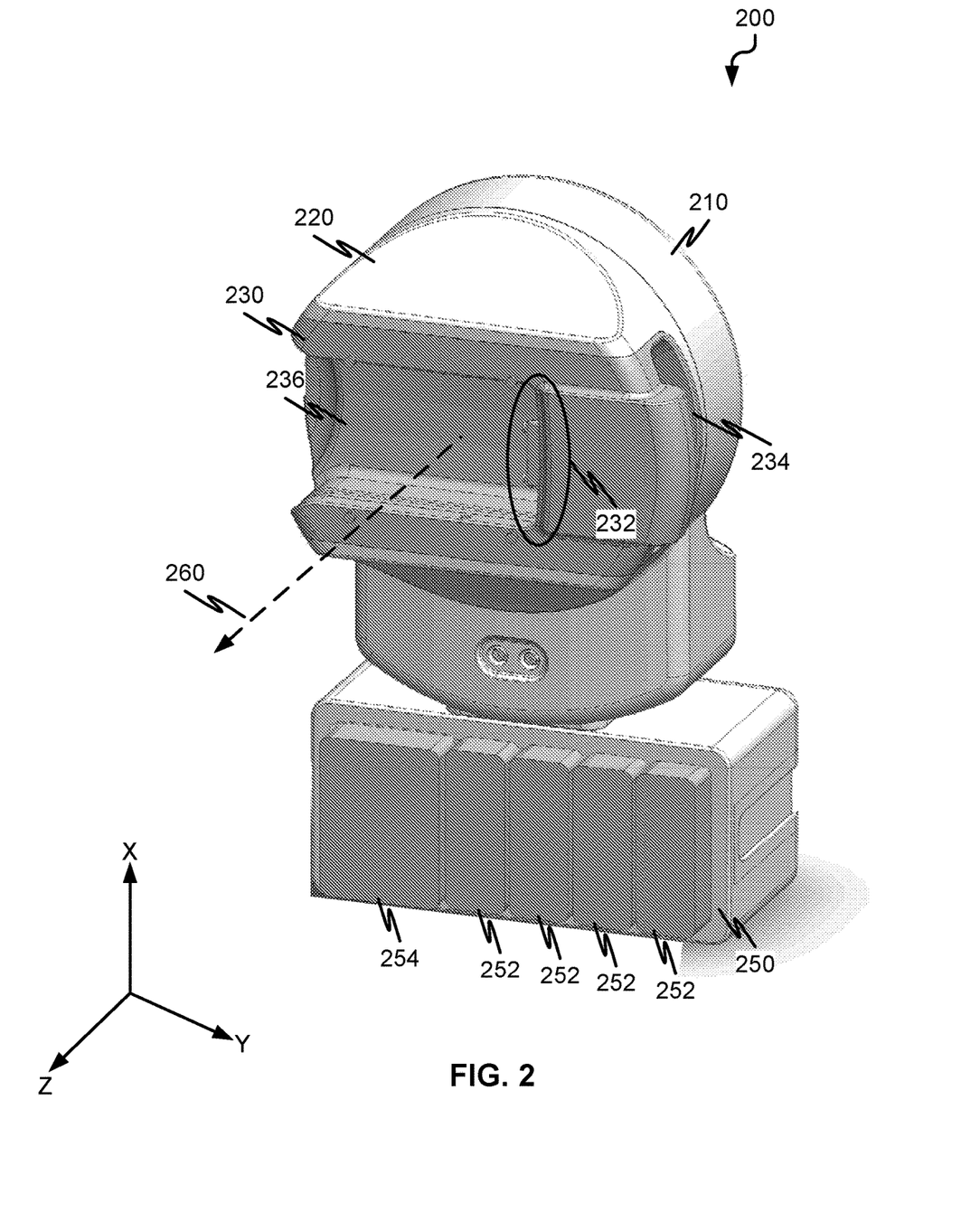
FIG. 2 is a perspective view of a rotatable docking station having a base component, rotational component, docking component, and physiological parameter measurement pod rack.

FIG. 2 is a perspective view of a rotatable docking station 200 having a base component 210, rotational component 220, docking component 230, and optional physiological parameter measurement pod rack 250. Base component 210 can include a rotational component 220 coupled thereto and an internal power supply (not shown) that can provide power to a detachably coupled monitor 120. Physiological parameter measurement pod rack 250 can include one or more bays for docking of one or more physiological parameter measurement pods 252, 254. Physiological parameter measurement pods 252, 254 are devices for measuring one or more patient physiological parameters. Additionally physiological parameter measurement pods 252, 254 can facilitate the exchange of data related to the physiological parameters with a patient monitoring device, such as monitor 120. Physiological parameter measurement pod rack 250 can also include additional input/output ports at the rear of its housing (not shown). When docked within physiological parameter measurement pod rack 250, the one or more physiological parameter measurement pods can transmit and/or receive data and/or power from physiological parameter measurement pod rack 250.

Docking component 230 can be coupled to rotational component 220. Docking component 230 can include a docking connector 232 and docking receptacle 236. A monitor 120, such as a patient monitoring device, can be docked within docking component 230 into docking receptacle 236. When docked into docking receptacle 236, monitor 120 can be locked into place by docking connector 232 and/or other mechanical features of docking component 230 (e.g., ledges, rails, ribs, abutments, latches, and the like to allow the monitor 120 to be secured within docking component 230). Docking connector 232 can facilitate the transfer of power and/or data between rotatable docking station 200 and a detachably coupled monitor 120.

Docking component 230 can also include a handle 234 located on one side opposite of the docking receptacle 236. Handle 234 can be ergonomically sized to accommodate various hand sizes (e.g., having an anthropometric profile between approximately 5th percentile to 95th percentile). A user can interact with handle 234, for example, via touching and/or gripping the handle (e.g., using a single hand) to circularly maneuverer the rotatable component 220. In some variations, handle 234 can include electrical and/or mechanical features to sense the touching and/or gripping of a user. Such electrical and/or mechanical features can prohibit movement of the rotational component 220 when a monitor 120 is docked within docking receptacle 236. Additionally, rotatable docking station 200 can have ergonomic radii that facilitates ease of cleaning.

Rotational component 220 can facilitate circular rotation about a center axis 260. Rotational component 220 can circularly maneuver about a 360 degree rotation axis (e.g., center axis 260) while base component 210 remains stationary. Such rotation can be in a clockwise and/or a counter-clockwise circular direction. In some variations, rotational component 220 can allow for circular maneuvering between an index position of 0 degrees and an index position of 180 degrees or 270 degrees due to various cable lengths of one or more cables 112. An index mechanism (not shown) internal to base component 210 and rotational component 220 can facilitate such rotational movement. Rotational component 220 can stop at various, clinically relevant index positions (e.g., spatially separated by approximately 90 degree increments about a 360 degree axis, spatially separated by approximately 45 degree increments about a 360 degree axis). Rotational component 220 facilitates positioning of a detachably coupled monitor 120 to a position convenient for patient monitoring. For example, such convenience can include the positioning of the monitor to accommodate placement of cables coupled to the monitor 120 or positioning of the monitor based on hand preference of the user (e.g., nurses, doctors, physician assistants, or any other person charged with providing a healthcare service to a patient). User interaction with handle 234 can engage and/or disengage a locking component within the internal index mechanism into the various index positions. In some variations, the internal index mechanism can be a mechanical mechanism having mechanical detent locking components at the various index positions. In other variations, the internal index mechanism can be a magnetic mechanism such as magnetic positional stops, as discussed in detail with FIGS. 3A-3B.

Figure 3A:
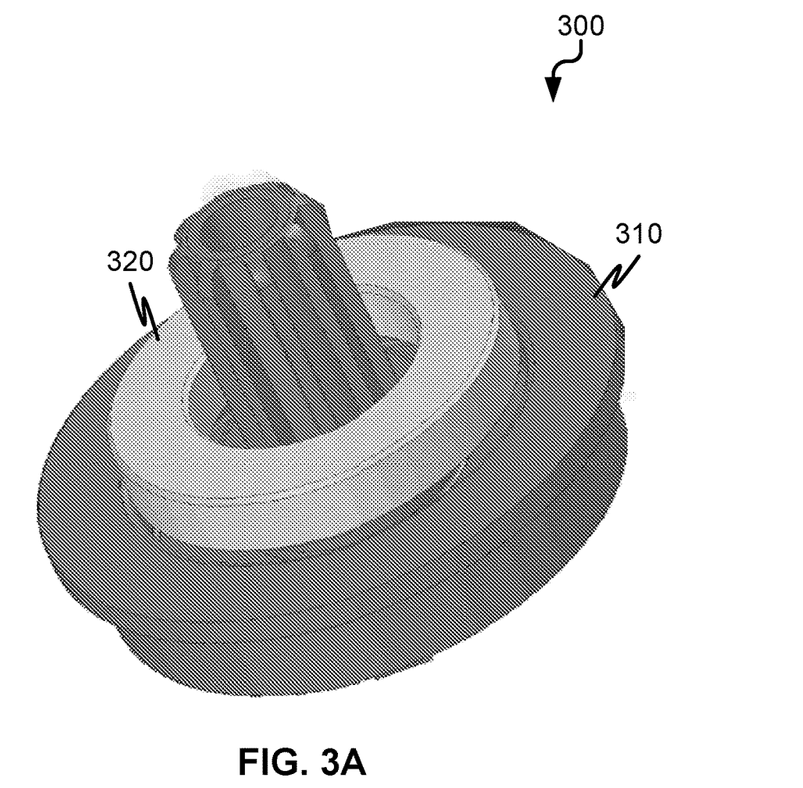
FIG. 3A is a perspective view of an example magnetic index mechanism.
Figure 3B:
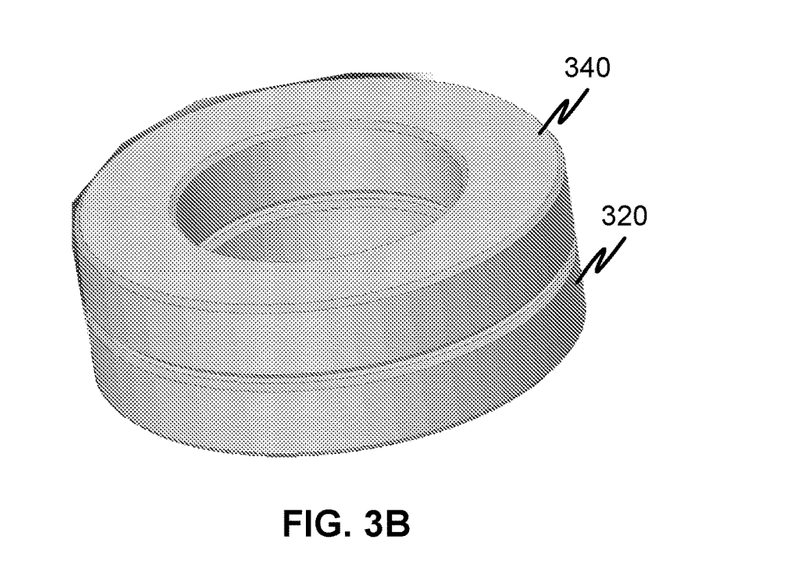
FIG. 3B is a perspective view of a first and second securing magnetic ring of the example magnetic index mechanism of FIG. 3A.

FIG. 3A is a perspective view of an example magnetic index mechanism 300 having magnetic positional stops at various index positions. Index mechanism 300 can include T-shaft 310 mounted within base component 210 and a first securing magnetic ring 320. First securing magnetic ring 320 can be correlated with second securing magnetic ring 340 of FIG. 3B. FIG. 3B is a perspective view of a first and second securing magnetic ring of the example magnetic index mechanism 300 of FIG. 3A. The second securing magnetic ring 340 can be internally mounted within rotational component 220. The first and second securing magnetic rings 320, 340 can be electromagnets, e.g., multi-pole correlated magnetic structures, that are pre-programmed to result in varying resistance as they are rotated with respect to one another. The magnetic attraction between the first securing magnetic ring 320 and second securing magnetic ring 340 can facilitate the rotational movement of rotational component 220. The magnetic interaction between the first and second securing magnetic rings 320, 340 can replicate a tactile feeling (to a user) of a spring force that acts against the rotation of rotatable component 220. Such tactile feeling can represent a torsional resistance felt by a user that increases as the rotational component 220 approaches one of the index positions (e.g., 45 or 90 degree increments of a 360-degree axis).

Figure 4A:
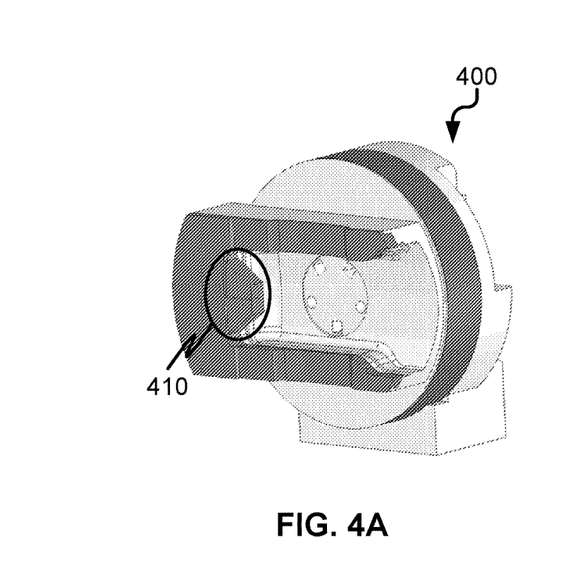
FIGS. 4A-4C are perspective views of a rotatable docking station having a sliding shroud.
Figure 4B:
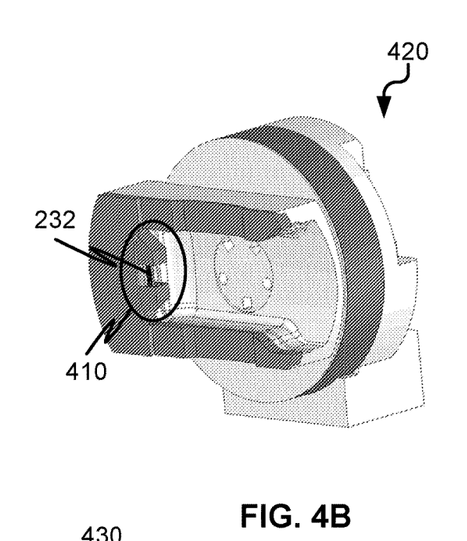
Figure 4C:
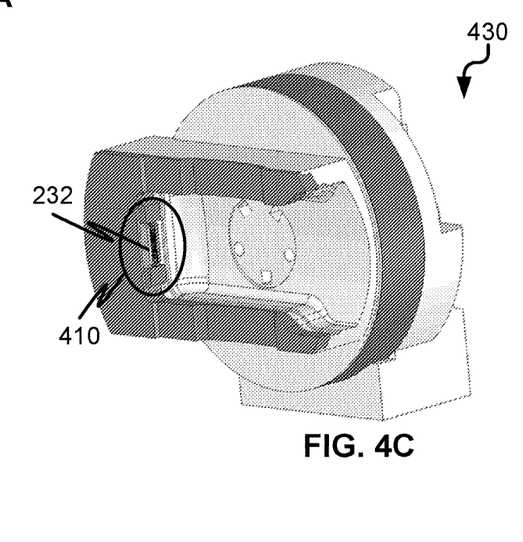

FIGS. 4A-4C are perspective views 400, 420, 430 of a rotatable docking station 400 having a sliding shroud 410. As illustrated in FIG. 4A, sliding shroud 410 can cover at least a portion of docking receptacle 236 in absence of a monitor 120 being docked within docking receptacle 236, in order to prevent particle and/or liquid contamination. For example, such contamination can be caused by an ingress of moisture and/or particulates, such as dust and/or water. More specifically, the sliding shroud 410 can protect the docking connecter 232 within docking receptacle 236. The protection provided by sliding shroud 410 can facilitate electrical connections between a monitor 120 and docking connector 232. Sliding shroud 410 can cover at least a portion of docking connecter 232, for example, when rotatable docking station 160 is not in use. Sliding shroud 410 can retract into the docking receptacle 236 towards docking connector 232 in order to expose docking connector 232 when a monitor 120 is being coupled to docking receptacle 236. For example, an act by a user to mount a monitor 120 into docking receptacle 236 can cause sliding shroud 410 to mechanically retract into docking receptacle 236, absent any additional act by the user, so as to expose docking connector 232, as illustrated in perspective view 420 of FIG. 4B. For illustration purposes, FIG. 4B illustrates a transitional view of sliding shroud 410 partially retracted to expose a portion of docking connector 232. When monitor 120 is fully docked within docking receptacle 236, sliding shroud 410 can fully expose docking connector 232, as illustrated in perspective view 430 of FIG. 4C. The direct mechanical force of monitor 120 being docked within docking receptacle 236 causes sliding shroud 410 to retract into docking receptacle 236, exposing docking connector 232. Sliding shroud 410 can include one or more spring mechanisms which facilitate covering of docking connector 232 when monitor 120 is absent from docking receptacle 236. The one or more spring mechanisms internal to the sliding shroud 410 can be compressed during the docking of the monitor 120 within docking receptacle 236. Note that for illustration purposes, the monitor 120 that is being docked within docking receptacle 236 is not illustrated in FIG. 4B or FIG. 4C. When the monitor 120 is removed from docking receptacle 236, the one or more spring mechanisms within sliding shroud 410 decompress, causing the sliding shroud 410 to cover docking connector 232 as illustrated in FIG. 4A.

Figure 5:
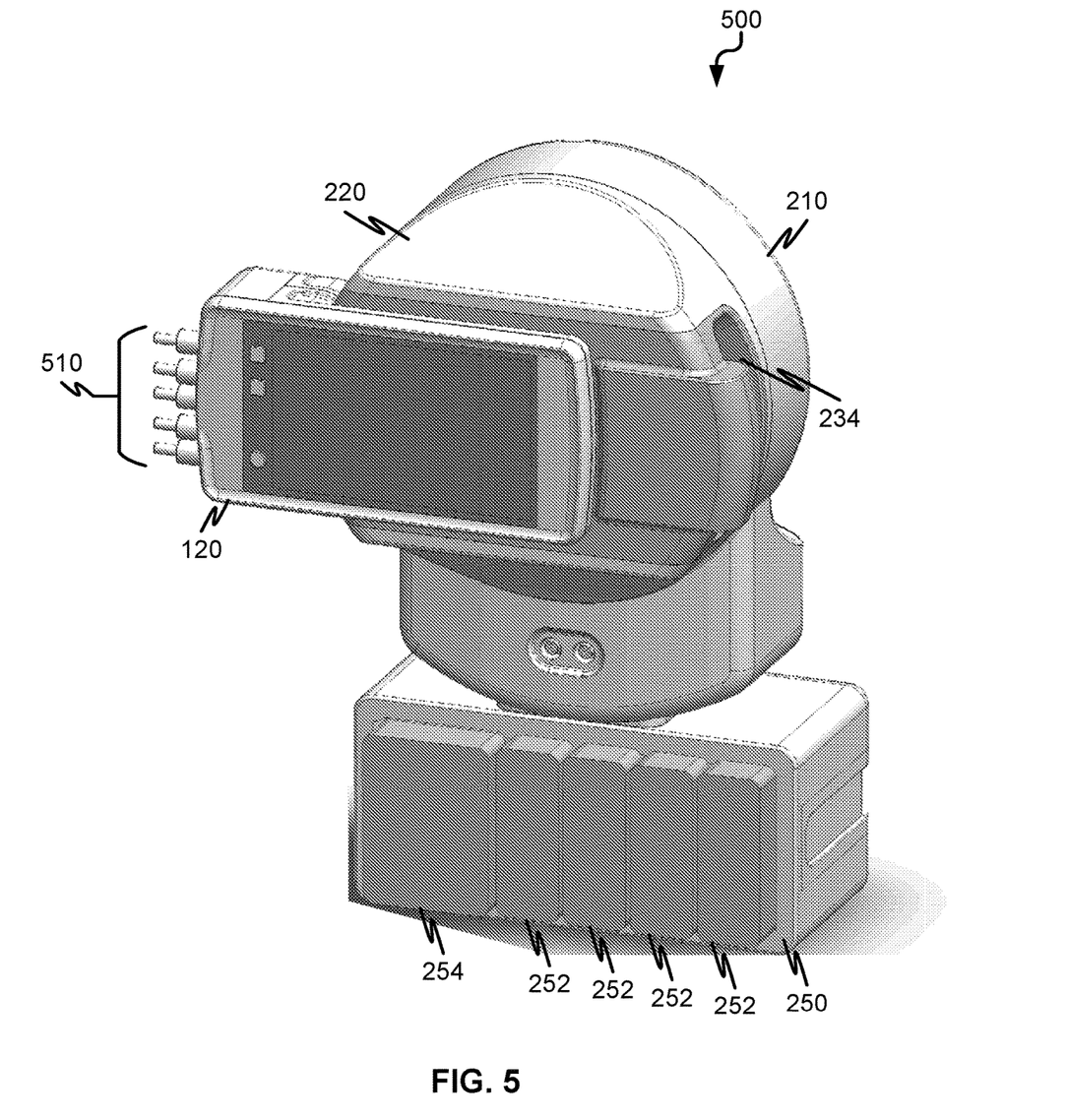
FIG. 5 is a perspective view of an example rotatable docking station having a monitor detachably coupled to docking receptacle of FIG. 2 at an index position of 0 degrees.

FIG. 5 is a perspective view of an example rotatable docking station 500 having a monitor 120 detachably coupled to docking receptacle 236 of FIG. 2 indexed at a 0 degree position. As illustrated in FIG. 5, monitor 120 is positioned such that one or more connection ports 510 are on the left hand side of rotatable docking station 500. Such orientation can facilitate, for example, a right-handed touching and/or gripping of handle 234 to circularly maneuver the rotational component 220 to another index position. The one or more cables 112 can be coupled to the one or more connection ports 510 to facilitate transmission of physiological parameters of patient 110 to monitor 120.

Figure 6:
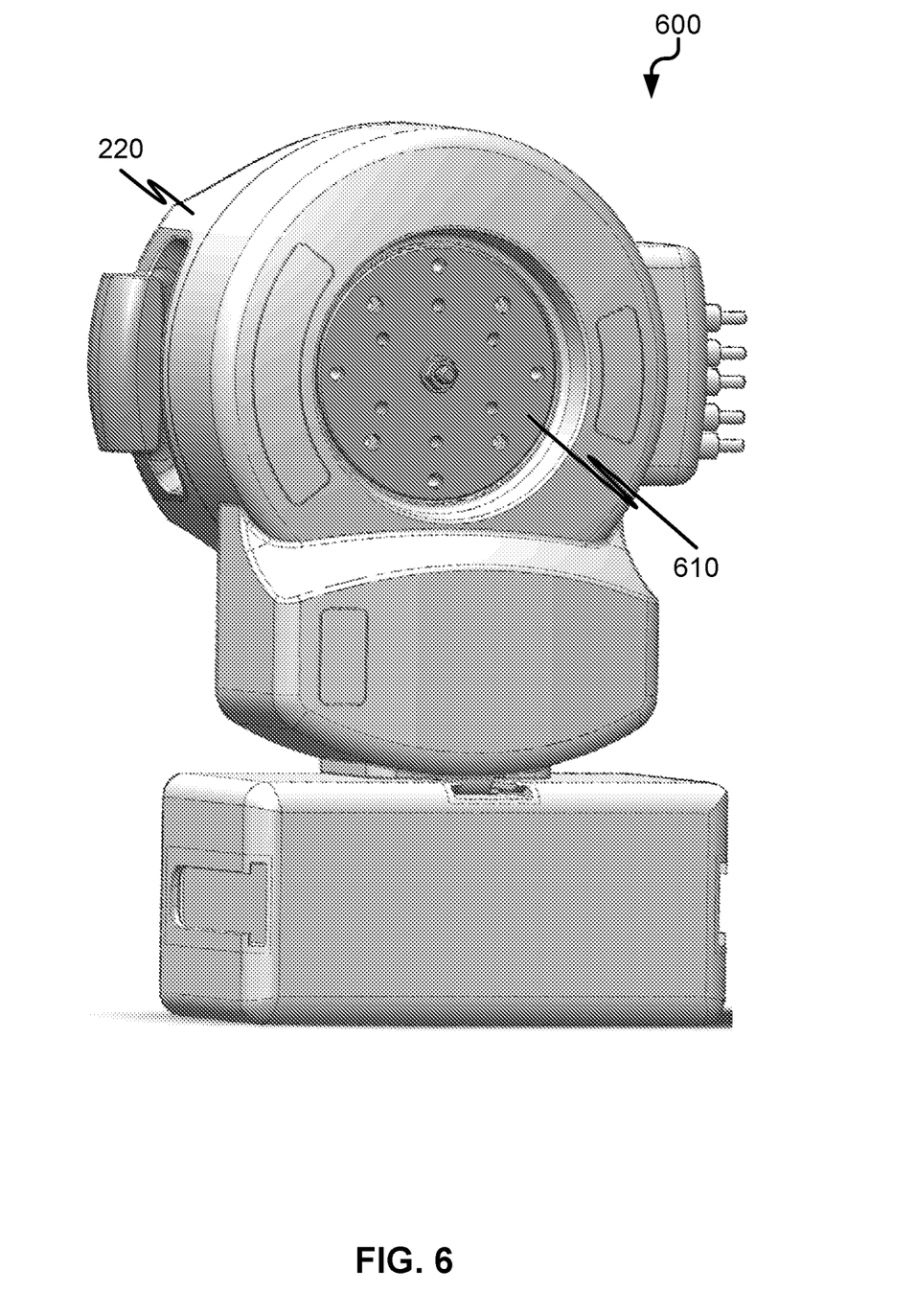
FIG. 6 a rear view of the rotatable docking station of FIG. 5.

FIG. 6 a rear view 600 of the rotatable docking station 500 of FIG. 5. Plate 610 can provide support for the weight of the rotational component 220. Plate 610, in some variations, can be a metal plate. A mounting interface, such as a universal mounting interface, can couple the plate 610 to a mounting point such as a wall.

Figure 7:
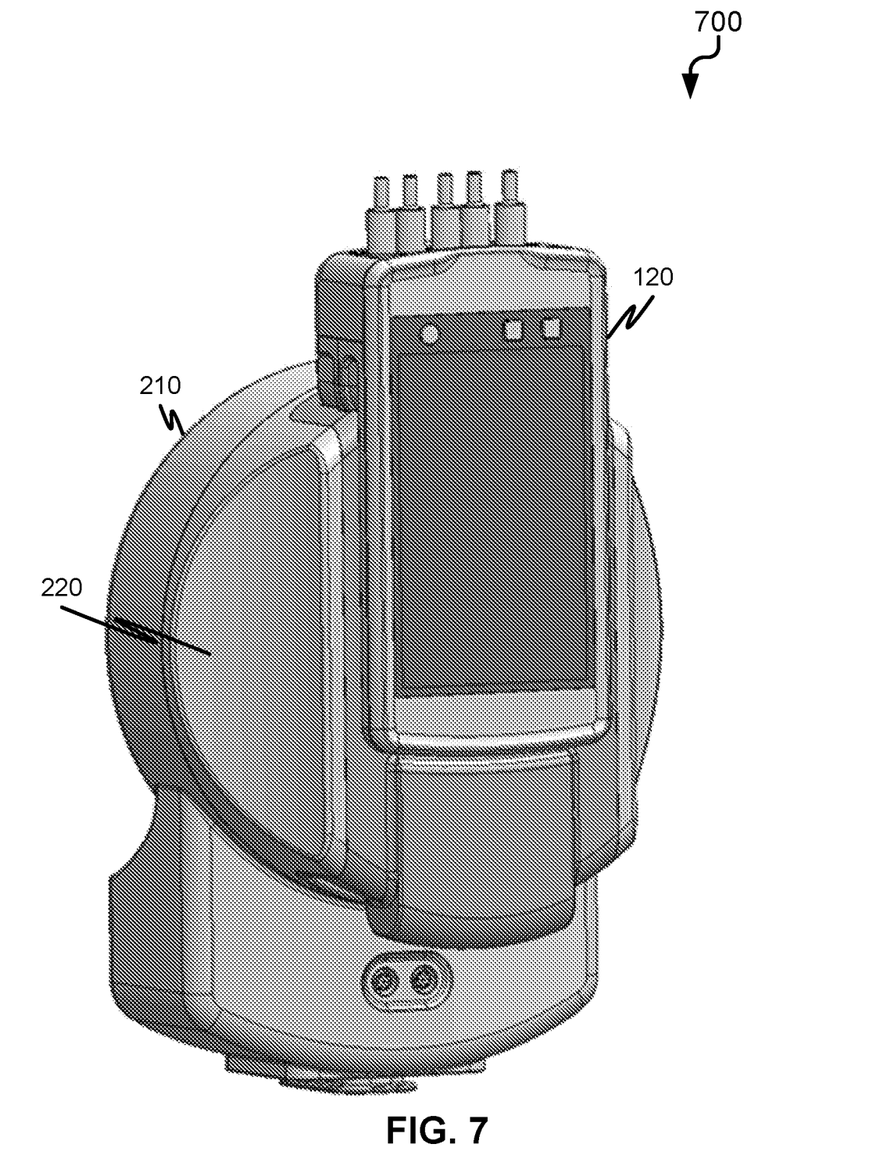
FIG. 7 is a perspective view of a rotatable docking station having a monitor detachably coupled to docking receptacle of FIG. 2 at an index position of 90 degrees.

FIG. 7 is a perspective view of a rotatable docking station 700 having a monitor 120 detachably coupled to docking receptacle 236 of FIG. 2 at an index position of 90 degrees.

Figure 8:
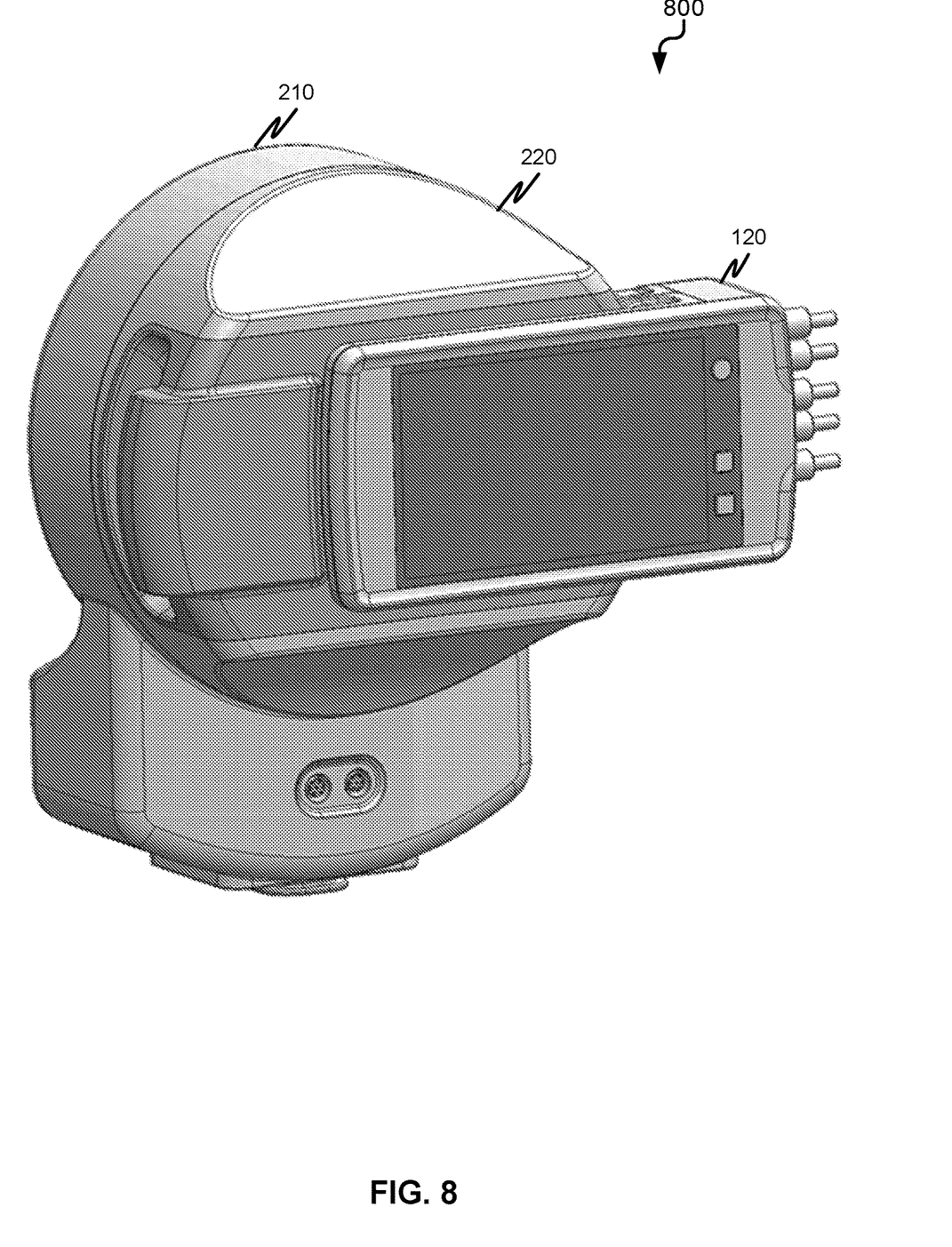
FIG. 8 is a perspective view of a rotatable docking station having a monitor detachably coupled to docking receptacle of FIG. 2 at an index position of 180 degrees.

FIG. 8 is a perspective view of a rotatable docking station 800 having a monitor 120 detachably coupled to docking receptacle 236 of FIG. 2 at an index position of 180 degrees.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system can include clients and servers. A client and server are generally remote from each other and typically interact through a communication network. The relationship of client and server arises by virtue of computer programs running on the respective computers and having a client-server relationship to each other. The computing systems/devices can include a variety of devices including personal computers, mobile phones, tablet computers, and Internet-of-Things (IoT) devices.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "computer-readable medium" refers to any computer program product, apparatus and/or device, such as for example magnetic discs, optical disks, solid-state storage devices, memory, and Programmable Logic Devices (PLDs), used to provide machine instructions and/or data to a programmable data processor, including a computer-readable medium that receives machine instructions as a computer-readable signal. The term "computer-readable signal" refers to any signal used to provide machine instructions and/or data to a programmable data processor. The computer-readable medium can store such machine instructions non-transitorily, such as for example as would a non-transient solid-state memory or a magnetic hard drive or any equivalent storage medium. The computer-readable medium can alternatively or additionally store such machine instructions in a transient manner, for example, as would a processor cache or other random access memory associated with one or more physical processor cores.

To provide for interaction with a user, the subject matter described herein can be implemented on a computer having a display device (e.g., a CRT (cathode ray tube) or LCD (liquid crystal display) monitor) for displaying information to the user and a keyboard and a pointing device (e.g., a mouse or a trackball) and/or a touch-screen by which the user can provide input to the computer. Other kinds of devices can be used to provide for interaction with a user as well; for example, feedback provided to the user can be any form of sensory feedback (e.g., visual feedback, auditory feedback, and/or tactile feedback); and input from the user can be received in any form, including acoustic, speech, or tactile input.

In the descriptions above and in the claims, phrases such as "at least one of" or "one or more of" can occur followed by a conjunctive list of elements or features. The term "and/or" can also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations can be within the scope of the following claims.

What is claimed is:

1. An apparatus for orientating a patient monitor, the apparatus comprising:
    a docking receptacle configured to receive the patient monitor, the docking receptacle including a docking connector for interfacing with the patient monitor;
    a handle configured to enable a user to orient the patient monitor to two or more index positions; and
    a base component coupled to the docking receptacle and configured to provide support to the docking receptacle;
    wherein:
        the docking receptacle is configured to maneuver between a plurality of index positions, the plurality of index positions including the two or more index positions; and
        the patient monitor includes an electronic visual display for displaying patient parameters.

2. The apparatus of claim 1, wherein the plurality of index positions includes 90-degree increments about a 360-degree axis.

3. The apparatus of claim 1, wherein a first index position of the plurality of index positions is zero degrees and a second index position of the plurality of index positions is 180 degrees.

4. The apparatus of claim 3, wherein a third index position of the plurality of index positions is 90 degrees.

5. The apparatus of claim 4, wherein a fourth index position of the plurality of index positions is 270 degrees.

6. The apparatus of claim 1, wherein an outer peripheral edge of the patient monitor interfaces with the docking receptacle.

7. The apparatus of claim 1, further comprising a power supply internal to the base component, the power supply being configured to provide power to the patient monitor when the patient monitor is docked in the docking receptacle.

8. The apparatus of claim 1, further comprising a sliding shroud configured to cover at least a portion of the docking receptacle when the patient monitor is not docked in the docking receptacle.

9. The apparatus of claim 8, wherein the sliding shroud is configured to protect the docking connector within the docking receptacle.

10. The apparatus of claim 9, wherein the sliding shroud is further configured to retract into the docking receptacle towards the docking connector so as to expose the docking connector.

11. The apparatus of claim 1, further comprising a rotational component that is configured to stop and prohibit movement of the docking receptacle to other index positions of the plurality of index position when the patient monitor is docked in the docking receptacle and locked at one of the plurality of index positions.

12. The apparatus of claim 11, wherein the docking receptacle is lockable at the plurality of index positions via respective mechanical positional stops.

13. The apparatus of claim 12, further comprising an index mechanism of the rotational component that is internal to the base component and configured to enable rotational movement while also providing the mechanical stops.

14. The apparatus of claim 1, further comprising an electrical connection to the base component, the electrical connection being configured to perform at least one of:
    providing power to the patient monitor; and
    facilitating transmission of data to the patient monitor.

15. The apparatus of claim 1, further comprising one or more sensors configured to measure at least one of an ECG (electrocardiogram), SPO2, blood pressure, apnea, and respiration.

16. The apparatus of claim 1, wherein the plurality of index positions includes 45-degree increments about a 360 degree axis.

* * * * *